United States Patent [19]
Bradbury et al.

[11] Patent Number: 5,198,434
[45] Date of Patent: Mar. 30, 1993

[54] ANGIOTENSIN II ANTAGONIZING FUSED PYRIDINYLOXY CONTAINING DERIVATIVES

[75] Inventors: Robert H. Bradbury, Wilmslow; David A. Roberts, Congleton, both of England

[73] Assignee: Imperial Chemical Industries PLC, London, England

[21] Appl. No.: 834,031

[22] Filed: Feb. 11, 1992

[30] Foreign Application Priority Data

Feb. 11, 1991 [GB] United Kingdom ............. 9102804.3

[51] Int. Cl.[5] ................. A61K 31/435; C07D 471/04; C07D 491/052
[52] U.S. Cl. .................... 514/215; 514/233.8; 514/234.5; 514/300; 514/301; 514/302; 540/523; 540/580; 544/127; 544/238; 544/333; 544/362; 544/405; 546/113; 546/114; 546/116; 546/122; 546/123
[58] Field of Search ............... 546/113, 114, 116, 122, 546/123; 540/523, 580; 544/127, 238, 333, 362, 405; 514/215, 233.8, 234.5, 300, 301, 302

[56] References Cited

U.S. PATENT DOCUMENTS

| | | | |
|---|---|---|---|
| 4,880,804 | 11/1989 | Carini et al. | 514/234.5 |
| 4,920,131 | 4/1990 | Huang et al. | |
| 5,028,615 | 6/1991 | Huang et al. | |
| 5,126,344 | 6/1992 | Roberts et al. | |
| 5,130,318 | 7/1992 | Roberts et al. | |

FOREIGN PATENT DOCUMENTS

| | | |
|---|---|---|
| 0315399 | 5/1989 | European Pat. Off. |
| 0326328 | 8/1989 | European Pat. Off. |
| 0326330 | 8/1989 | European Pat. Off. |
| 0348155 | 12/1989 | European Pat. Off. |
| 0412848 | 2/1991 | European Pat. Off. |
| 0445811 | 9/1991 | European Pat. Off. |
| 0475206 | 3/1992 | European Pat. Off. |
| WO91/07404 | 5/1991 | PCT Int'l Appl. |
| WO91/19697 | 12/1991 | PCT Int'l Appl. |

OTHER PUBLICATIONS

G. R. Proctor, et al., "Azabenzocycloheptenones. Part XIV. Cyclisation of Amino-acid Derivatives to Tetrahydro-1-benzazepin-5-ones and Tetrahydroquinolin-4-ones" *J. Chem. Soc., Perkin Trans. I* (1972), 1803–8.

R. D. Youssefyeh, et al. (principal author Huang) *J. Med. Chem.* (1990), 33, 1186–1194; *Chem. Abstr.* (1990), 112, 17, abstract 131,890u.

F-C. Huang *J. Med. Chem.* (1990), 33, 1194–1200.

*Primary Examiner*—Bernard Dentz
*Attorney, Agent, or Firm*—Thomas E. Jackson

[57] ABSTRACT

The invention concerns pharmaceutically useful compounds of the formula I, in which $R^1$, $R^2$, $R^3$, $R^4$, n, m, X, Y and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

10 Claims, No Drawings

ANGIOTENSIN II ANTAGONIZING FUSED PYRIDINYLOXY CONTAINING DERIVATIVES

This invention concerns novel heterocyclic derivatives and, more particularly, novel pyridine derivatives which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

In our co-pending European Patent Applications, Publication Nos. 412848, 453210 and 454831 there are respectively disclosed certain quinoline, pyridine and naphthyridine derivatives which have AII antagonist activity.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a pyridine derivative of the formula I (set out hereinafter, together with the other chemical formulae identified by Roman numerals) wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; $R^2$ is hydrogen, (1-8C)alkyl, (3-8C)cycloalkyl, (3-8C)cycloalkyl-(1-4C)alkyl, carboxy, (1-4C)alkoxycarbonyl, (3-6C)alkenyloxycarbonyl, cyano, nitro, phenyl or phenyl(1-4C)alkyl; $R^3$ is hydrogen or (1-4C)alkyl; $R^4$ is independently selected from hydrogen, (1-4C)alkyl, (1-4C)alkoxy, halogeno, trifluoromethyl, cyano and nitro; n and m are independently selected from zero or the integer 1 to 4 such that the number of methylene groups may optionally be replaced by a carbonyl group; Y is 2, 3 or 4, one of which methylene groups may optionally be replaced by a carbonyl group; Y is an oxygen atom, or a group of the formula —S(O)$_p$— or —NR— in which p is zero or the integer 1 or 2, and R is hydrogen, (1-8C)alkyl, (1-8C)alkanoyl, carbamoyl, N-alkylcarbamoyl and di-(N-alkyl)carbamoyl of up to 7 carbon atoms, phenyl, phenyl(1-4C)alkyl or substituted (1-4C)alkyl, the latter containing one or more fluoro substituents; or R is a group of the formula -A$^1$.A$^2$.B wherein A$^1$ is a direct bond or a carbonyl group; A$^2$ is (1-6C)alkylene; and B is selected from hydroxy, (1-4C)alkoxy, phenyloxy, phenyl(1-4C)alkoxy, pyridyl(1-4C)alkoxy, 4-morpholino(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino (—NH.SO$_2$.NH$_2$), carboxamidomethylamino (—NH.CH$_2$.CO.NH$_2$), (1-4C)alkanoyloxy, phenylcarbonyloxy, aminocarbonyloxy (—O.CO.NH$_2$), (1-4C)alkylaminocarbonyloxy, carboxy, (1-4C)alkoxycarbony, carbamoyl, N-alkylcarbamoyl and di-(N-alkyl)carbamoyl of up to 7 carbon atoms, (1-4C)alkanoyl, 4-morpholino, 1-imidazolyl and succinimido group; or B is a group of the formula -A$^3$.B$^1$ wherein A$^3$ is oxy, oxycarbonyl or imino and B$^1$ is a 5 or 6-membered saturated or unsaturated heterocyclic ring containing 1 or 2 nitrogen atoms and linked to A$^3$ by a ring carbon atom; or A$^3$ is oxycarbonyl and B$^1$ is a 4-morpholino group or a 5 or 6-membered saturated heterocyclic ring containing 1 or 2 nitrogen atoms, optionally bearing a (1-4C)alkyl group and linked to A$^3$ by a ring nitrogen atom; and wherein B$^1$ the remainder of the ring atoms are carbon; X is phenylene optionally bearing a substituent selected from (1-4C)alkyl, (1-4C)alkoxy, halogeno, trifluoromethyl, cyano and nitro, or X is a direct bond between the adjacent phenyl group and the carbon atom bearing $R^3$; Z is 1H-tetrazol-5-yl, —CO.NH.(1H-tetrazol-5-yl) or a group of the formula —CO.OR$^5$ or —CO.NH.SO$_2$.R$^6$ in which $R^5$ is hydrogen or a non-toxic, biodegradable residue of a physiologically acceptable alcohol or phenol, and $R^6$ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or an N-oxide thereof; or a non-toxic salt thereof.

It will appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ or $R^2$ when it is alkyl is, for example, methyl, ethyl, propyl, butyl, isobutyl, sec-butyl, pentyl or hexyl; and when it is cycloalkyl is, for example, cyclopropyl, cyclopentyl or cyclohexyl.

A particular value for $R^1$ when it is alkyl bearing one or more fluoro substituents is, for example, fluoromethyl, trifluoromethyl, 2,2,2-trifluoroethyl or pentafluoroethyl; and when it is alkyl bearing a cycloalkyl, (1-4C)alkoxy or phenyl substituent is, for example, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl; and when it is phenylalkyl is, for example, benzyl, 1-phenylethyl or 2-phenylethyl; when it is alkoxycarbonyl is, for example, methoxycarbonyl, ethoxycarbonyl or propoxycarbonyl; and when it is alkenyloxycarbonyl is, for example, allyloxycarbonyl, 2-methyl-2-propenyloxycarbonyl or 3-methyl-3-butenyloxycarbonyl.

A particular value for $R^3$, when it is alkyl is, for example, methyl or ethyl.

A particular value for $R^4$ or for an optional substituent which may be present when X is phenylene, when it is alkyl is, for example, methyl or ethyl; when it is halogeno is, for example, fluoro, chloro, bromo or iodo; and when it is alkoxy is, for example, methoxy or ethoxy.

Particular values for R include, by way of example, for alkyl: methyl, ethyl, propyl, butyl, isobutyl, sec-butyl, pentyl and hexyl; for alkanoyl: formyl, acetyl, propionyl, butyryl, pentanoyl and hexanoyl; for N-alkylcarbamoyl: N-methyl and N-ethylcarbamoyl; for di(N-alkyl)carbamoyl: N,N-dimethylcarbamoyl and N,N-diethylcarbamoyl; for phenylalkyl: benzyl, 1-phenylethyl and 2-phenylethyl; and for alkyl bearing one or more fluoro substituents: fluoromethyl, trifluoromethyl, 2,2,2-trifluoroethyl and pentafluoroethyl.

A particular value for $A^2$ is, for example, methylene, ethylene, trimethylene or tetramethylene, in any of which one methylene may bear 1 or 2 methyl substituents.

Particular values for B include, by way of example, for alkoxy: methoxy, ethoxy and isopropoxy; for phenylalkoxy: benzyloxy and phenethyloxy; for pyridylalkoxy: 2-pyridylmethoxy, 3-pyridylmethoxy, 4-pyridylmethoxy and 3-pyridylethoxy; for 4-morpholinoalkoxy: 4-morpholinomethoxy and 4-morpholinoethoxy; for alkylamino: methylamino, ethylamino and butylamino; for dialkylamino: dimethylamino, diethylamino and dipropylamino; for alkanoylamino: formamido, acetamido and propionylamido; for alkylsulphonylamino: methylsulphonylamino and ethylsulphonylamino; for alkanoyloxy: acetyloxy and propionyloxy; for alkylaminocarbonyloxy: methylaminocarbonyloxy and ethylaminocarbonyloxy; for alkoxycarbonyl: methoxycarbonyl, ethoxycarbonyl and propoxycarbonyl; for N-alkylcarbamoyl: N-methyl and N-ethylcarbamoyl; for di(N-alkyl)carbamoyl: N,N-dimethylcarbamoyl and N,N-diethylcarbamoyl; and for alkanoyl: formyl, acetyl and propionyl.

A particular value for $B^1$ when it is a 5 or 6-membered unsaturated heterocyclic ring containing 1 or 2 nitrogen atoms is, for example, pyrrolyl, imidazolyl, pyrazolyl, pyridyl, pyrazinyl, pyrimidinyl or pyridazinyl; and when it is a 5 or 6-membered saturated heterocyclic ring containing 1 or 2 nitrogen atoms is, for example, pyrrolidinyl, imidazolidinyl, pyrazolinyl, piperidinyl or piperazinyl.

A particular value for an alkyl group which may be present on $B^1$ when it is a 5 or 6-membered saturated heterocyclic ring is, for example, methyl or ethyl.

A particular value for $R^5$ when it is a non-toxic, biodegradable residue of a physiologically acceptable alcohol or phenol is, for example, a residue derived from a (1-6C)alkanol such as methanol or ethanol, or phenol, glycerol or the like.

A particular value for $R^6$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on phenyl moieties include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^1$ is, for example, methyl or ethyl, of which the latter is particularly preferred.

A preferred value for $R^2$, $R^3$ and $R^4$ is, for example, hydrogen.

A preferred value for $R^5$ is, for example, hydrogen.

A preferred value for Y is, for example, an oxygen atom or a group of the formula —NR—.

A preferred value for R includes, for example, hydrogen, (1-8C)alkyl (especially methyl), (1-8C)alkanoyl (especially acetyl) and phenyl(1-4C)alkyl (especially benzyl).

A preferred combination of values for n and m includes, for example, when the sum of n and m is 3; and in particular when n is 2 and m is 1; and when n is 1 and m is 2.

A preferred value for Z is, for example, 1H-tetrazol-5-yl and which is especially preferred when attached ortho to the group X.

A group of compounds of the invention which is of particular interest comprises those compounds of the formula I wherein X is p-phenylene; Z is 1H-tetrazol-5-yl; and $R^1$, $R^2$, $R^3$, $R^4$, Y, n and m have any of the meanings defined above; and the non-toxic salts thereof. Preferably within this group the tetrazole group is ortho to the adjacent phenyl ring.

A group of compounds of the invention which is of special interest comprises those compounds of the formula Ia wherein one of $Y^1$ and $Y^2$ is an oxygen atom or a group of the formula —NR— as defined above and the other is a methylene (—CH$_2$—) group; $R^7$ is hydrogen, (1-4C)alkyl, (1-4C)alkoxy, halogeno, trifluoromethyl, cyano or nitro; and $R^1$, $R^2$ and $R^4$ have any of the meanings given above; and the non-toxic salts thereof. Preferably within this group the tetrazole group is ortho to the adjacent phenyl ring. Within this group it is especially preferred that one of $Y^1$ and $Y^2$ is oxygen and the other is methylene.

Compounds of the invention which are of particular interest include, for example, the specific embodiments set out hereinafter in the accompanying Examples. Of these, the compounds of formula I described in Examples 2 and 10 are of special interest and these compounds, or a non-toxic salt thereof, are provided as a further feature of the invention.

Although all of the formula I compounds can form salts with suitable acids, it will be appreciated that those compounds of formula I wherein Z is other than an ester group or in which R or $R^2$ bear a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —$CO.OR^5$ in which $R^5$ is hydrogen), a carboxylic acid derivative of the formula II, in which Q is a protected carboxy group selected from (1-6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1-4C)alkanol, such as aqueous methanol or ethanol. However, it may also be performed in a mixture of an aqueous and non-aqueous solvent such as water and toluene using a conventional quaternary ammonium phase transfer catalyst. The hydrolysis is generally performed at a temperature in the range, for example, 0°-120° C., depending on the reactivity of the group Q. In general, when Q is carbamoyl, temperatures in the range, for example, 40°-120° C. are required to effect the hydrolysis.

Alternatively, when Q is benzyloxycarbonyl the conversion may also be performed by hydrogenolysis, for example using hydrogen at 1-3 bar in the presence of a suitable catalyst, such as palladium on charcoal or on calcium sulphate, in a suitable solvent or diluent such as a (1-4C)alkanol (typically ethanol or 2-propanol) and at a temperature in the range, for example, 0°-40° C.

Further, when Q is t-butoxycarbonyl, the conversion may also be carried out by hydrolysis at a temperature in the range, for example, 0°-100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example trimethyltin or tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a nitrile of the formula IX with a trialkyltin azide, such as tributyltin azide, or triphenyltin azide respectively. The reaction is conveniently carried out in a suitable solvent or diluent, such as toluene or xylene, and at a temperature in the range, for example, 50°-150° C. The nitriles of the formula IX may be obtained, for example, by alkylation of a pyridone of the formula IV wherein $R^1$ is other than hydrogen with a nitrile of the formula X wherein Hal. stands for a suitable leaving group such as chloro, bromo, iodo, methanesulphonyloxy or p-toluenesulphonyloxy, using similar conditions to those used in process (c) described hereinafter. The necessary compounds of formula X may be made by standard procedures such as that illustrated in Scheme 1 for compounds in which X is phenylene, or from a compound of the formula XI using methods of organic chemistry well known in the art. Alternatively, the nitriles of the formula IX may be obtained from stepwise conversion of a compound of formula I wherein Z is a group of the formula —$CO.OR^5$ under standard conditions.

The nitriles of the formula IX may also be obtained, for example, by reaction of a pyridine of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) with an alcohol of the formula XI, using similar conditions to those used in process (d) described hereinafter. The alcohol of the formula XI may be obtained, for example, by standard procedures such as that illustrated in Scheme 1 for compounds in which X is phenylene, or by analogy with Scheme 2 starting with a compound of the formula X.

Alternatively, compounds of the formula III may be obtained, for example, by reaction of a pyridine of the formula VII wherein $Y^1$ is as defined above with an alcohol of the formula XII under similar conditions to those described in process (d) hereinafter. The alcohols of formula XII may be obtained, for example, from the appropriate bromomethyl compound by standard procedures, or analogy therewith, such as those shown in Scheme 2.

It will be appreciated that compounds of the formula III wherein X is the group —NR— in which R is other than hydrogen may be obtained by subsequent modification of a compound of the formula III wherein X is the group —NR— in which R is hydrogen previously prepared using one of the methods described herein. Such modification may be carried out using standard procedures of organic chemistry well known in the art. For example, reductive alkylation may be used to obtain compounds of the formula III wherein X is the group —NR— in which R is an alkyl group and conventional acylation procedures, for example using a carboxylic acid halide or anhydride, may be used to obtain compounds of the formula III wherein X is the group —NR— wherein R is an alkanoyl group.

c) A pyridone of the formula IV wherein $R^1$ is other than hydrogen is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an alkali metal carbonate such as sodium or potassium carbonate, or an organic base such as diisopropylethylamine and in a suitable solvent or diluent, for example, a (1-4C)alkanol such as methanol or ethanol when an alkali metal alkoxide is used, or in a polar solvent such as N,N-dimethylformamide or N-methylpyrrolidone and at a temperature in the range, for example, 10°-100° C. Alternatively, a quaternary ammonium hydroxide may be used in a mixture of an aqueous and non-aqueous solvent such as water and dichloromethane. In carrying out process (c), when $R^5$ is hydrogen in the starting material of formula V, about two molecular equivalents of a suitable base is generally required, whereas when $R^5$ is other than hydrogen the presence of one molecular equivalent of a suitable base is generally sufficient.

Procedure (c) is particularly suitable for the production of those compounds of the formula I in which Z is a group of the formula —$CO.OR^5$ in which $R^5$ is other than hydrogen, for example wherein $R^5$ is (1-6C)alkyl, benzyl or phenyl, which compounds are also starting materials of formula II for the reaction described in (a) above. Similarly, using an analogous procedure, but starting with the appropriate halomethyl tetrazolyl derivative of the formula VI, the starting materials of the formula III may be obtained for procedure (b).

It will be appreciated that in the alkylation reaction of a compound of the formula IV wherein Y is an imino (—NH—) group with a compound of the formula V or VI (or with a compound of the formula X to give a nitrile of the formula IX) it may be preferable to protect Y prior to carrying out the alkylation, for example with a suitable protecting group such as trifluoroacetyl, whereafter the protecting group may be removed.

Certain of the pyridones of formula IV are already known and the remainder can be made by analogy therewith using standard procedures of organic chemistry well known in the art, for example as described in standard works of heterocyclic chemistry such as that edited by Elderfield, or as shown in Schemes 3 and 4 and for which the starting materials may be obtained, for example, using similar procedures to those described in (or by analogy with) *J. Org. Chem.*, 1985, 50, 2608; *J. Het. Chem.*, 1975, 12, 809; and *Arch. Pharm.*, 1984, 317, 958. The necessary compounds of the formula V (and also of formula VI) may be made by standard procedures such as those which are illustrated in Scheme 1 for compounds in which X is phenylene. Alternatively, a compound of the formula V or formula VI may be obtained from a formula VIII compound (in which Z is the group $CO.OR^5$) or formula XII compound respectively, using procedures of organic chemistry well known in the art.

Compounds of the formula VI wherein X is phenylene and $R^3$ is hydrogen may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(0) catalyst, such as tetrakis(triphenylphosphine)palladium, and azo(bisisobutyronitrile). The resultant substituted 4'-methyl-biphenylcarbonitrile may then be converted to a compound of the formula VI by carrying out steps (b), (c) and (d) in a similar manner to that shown in Scheme 1. Alternatively, suitably substituted 4'-methylbiphenylcarbonitriles may be obtained by reaction of a 4-methylphenylboronic acid with an appropriately substituted bromobenzonitrile in the presence of a suitable palladium catalyst, such as palladium (II)chloride or tetrakis(triphenylphosphine)palladium, and azo(bisisobutyronitrile).

d) A pyridine derivative of the formula VII wherein $Y^1$ is a suitable leaving group (such as chloro, bromo, iodo, methanesulphonyl, methanesulphonyloxy, p-toluenesulphonyloxy or trifluoromethanesulphonyloxy) is reacted with an alcohol of the formula VIII.

The reaction is generally carried out in the presence of a suitable base, for example an alkali metal alkoxide such as sodium methoxide or ethoxide or an alkali metal hydride such as sodium hydride and in a suitable solvent or diluent, for example a (1-4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. The reaction may in preference be carried out with a formula VIII compound in the presence of an acid catalyst such as p-toluenesulphonic acid, instead of under basic conditions, and in the presence of an inert solvent or diluent such as toluene. Yet a further alternative is to heat together a compound of the formula VII with a formula VIII compound at an elevated temperature, for example, at a temperature in the range 120°-180° C. and in the absence of solvent or in the presence of a high boiling solvent or diluent such as diphenyl ether.

Pyridine derivatives of the formula VII wherein $Y^1$ is halogeno may be obtained, for example, by halogenation of the corresponding pyridones of formula IV, for example, by reaction with phosphorus oxychloride in the absence of a solvent, or in the presence of an inert solvent or diluent such as toluene or dioxane, and at a temperature in the range 60°-110° C. Compounds of the formula VII wherein $Y^1$ is methanesulphonyloxy, p-toluenesulphonyloxy or trifluoromethanesulphonyloxy and $R^1$ and $R^3$ are other than hydrogen may be obtained, for example, by acylation of the corresponding pyridones of formula IV with the corresponding sulphonyl chloride under standard conditions. Compounds of the formula VII wherein $Y^1$ is methanesulphonyl may be obtained from alkylation of the corresponding mercaptopyridines followed by oxidation under standard conditions. The alcohols of the formula VIII are known or can be prepared by standard procedures well known in the art, for example, by analogy with Scheme 2 or deprotection of a compound obtained thereby.

Whereafter, those compounds of formula I wherein Z is 1H-tetrazol-5-yl may be obtained by stepwise conversion of a compound of the formula I wherein Z is a group of the formula —CO.OR$^5$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH. (1H-tetrazol-5-yl), a group of the formula —CO.NH.SO$_2$R$^6$ or a group of the formula —CO.OR$^5$ in which R$^5$ is other than hydrogen, may be obtained, for example, by reacting a carboxylic acid of the formula I in which Z is carboxy (or a reactive derivative of said acid) with 5-aminotetrazole, a sulphonamide of the formula NH$_2$.SO$_2$R$^6$ or a salt thereof (for example, an alkali metal salt), or a hydroxy compound of the formula HO.R$^5$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —CO.NH.SO$_2$R$^6$ or a group of the formula —CO.OR$^5$, the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°-60° C.

Whereafter, when an N-oxide derivative of a compound of the formula I is required, a compound of the formula I is oxidised. Suitable oxidising agents include those well known in the art for the conversion of nitrogen heterocycles to their corresponding N-oxide derivatives, for example, hydrogen peroxide or an organic peracid such as m-chloroperbenzoic acid or peracetic acid. The oxidation is preferably carried out in a suitable conventional solvent or diluent for such oxidations, for example dichloromethane, chloroform or acetic acid, and at a temperature in the general range, for example 0° to 80° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure, for example using an aqueous mineral acid such as dilute hydrochloric acid.

According to a further aspect of the invention, there is provided a process for the manufacture of a compound of the formula I wherein Z is tetrazolyl, X is p-phenylene optionally bearing a substituent selected from (1-4C)alkyl, (1-4C)alkoxy, halogeno, trifluoromethyl, cyano and nitro; R$^3$ is hydrogen; and R$^1$, R$^2$, R$^4$, Y, n and m have any of the meanings defined hereinbefore; which comprises reaction of a compound of the formula XIII wherein P$^1$ is an electron-deficient phenyl group or is a pyridyl or pyrimidyl group; R$^8$ is hydrogen, (1-4C)alkyl, (1-4C)alkoxy, halogeno, trifluoromethyl, cyano or nitro; and R$^1$, R$^2$, R$^3$, R$^4$, X, Y, n and m have any of the values defined above with a base selected from an alkali metal hydroxide, (1-12C)alkanolate, (1-12C)alkanethiolate, phenolate. thiophenolate and diphenylphosphide, wherein any phenyl ring of the latter three groups may optionally bear a (1-4C)alkyl, (1-4C)alkoxy or halogeno group.

A particular value for P$^1$ when it is an electron-deficient phenyl group includes, for example, a phenyl group bearing 1, 2 or 3 electron-withdrawing groups independently selected from halogeno (typically chloro or bromo), nitro, cyano and trifluoromethyl.

A particular value for R$^8$ when it is alkyl is, for example, methyl or ethyl; when it is alkoxy is, for example, methoxy or ethoxy; and when it is halogeno is, for example, fluoro, chloro, bromo or iodo.

Suitable bases are, by way of example:
for an alkali metal hydroxide: sodium or potassium hydroxide;
for an alkali metal alkanolate: an alkali metal (1-8C)alkanolate, for example an alkali metal (1-4C)alkoxide, such as sodium or potassium methoxide, ethoxide, propoxide or butoxide;
for an alkali metal alkanethiolate: an alkali metal (1-8C)alkanethiolate, for example an alkali metal (1-4C)alkanethiolate such as sodium or potassium methanethiolate, ethanethiolate. propanethiolate or butanethiolate.

A particular value for an optional substituent on a phenyl group of an alkali metal phenolate, thiophenolate or diphenylphosphide, when it is alkyl is, for example, methyl or ethyl; when it is alkoxy is, for example, methoxy or ethoxy; and when it is halogeno is, for example, fluoro, chloro or bromo.

A preferred value for P$^1$ is, for example, an electron-deficient phenyl group, especially a nitrophenyl group, in particular 4-nitrophenyl.

A preferred value for X is, for example, when it is unsubstituted p-phenylene.

A particularly preferred base is an alkali metal alkanethiolate such as sodium or potassium propanethiolate, an alkali metal alkanolate such as sodium or potassium ethoxide, or an alkali metal thiophenolate such as sodium or potassium 4-fluorothiophenolate.

It will be appreciated that when the base is an alkali metal alkanolate, alkanethiolate, phenolate, thiophenolate or diphenylphosphide, it may be generated in situ from the corresponding alkanol, alkanethiol, phenol, thiophenol or diphenylphosphine with a suitable alkali metal base such as an alkali metal hydride, for example, lithium, potassium or sodium hydride.

The process of the invention is particularly useful for the preparation of compounds of the formula I wherein the tetrazolyl group is at the ortho position relative to the adjacent phenyl group.

The reaction is conveniently carried out in a suitable inert organic solvent or diluent, for example, a polar solvent such as N,N-dimethylformamide or N-methylpyrrolidone. Alternatively, an alkanol such as methanol or ethanol may be used, for example, when an alkali metal hydroxide or alkoxide such as sodium or potassium hydroxide, methoxide or ethoxide is employed. The reaction is generally carried out at a temperature in the range, for example, $-30°$ C. to $50°$ C. It will be appreciated that the choice of temperature will depend on the nature of the base employed. For example, when an alkali metal alkanethiolate or alkanolate is used, a temperature in the range of $0°$ C. to ambient temperature is preferred.

Compounds of the formula XIII may be obtained by reaction of a boronic acid of the formula XIV with a compound of the formula XV wherein $P^1$ is an electron-deficient phenyl group having any of the meanings defined above and V is a bromo, iodo or trifluoromethanesulphonyloxy group, in the presence of a palladium(0) catalyst, such as tetrakis(triphenylphosphine)palladium, and azo(bisisobutyronitrile). The reaction is preferably carried out in the presence of a base, such as sodium or potassium carbonate, in an inert solvent or diluent, for example, a hydrocarbon such as toluene or xylene, an ether, such as dioxan or tetrahydrofuran, an (1-4C)alkanol such as methanol or ethanol, water, or mixture thereof, for example a mixture of water, methanol and toluene, and at a temperature in the range of, for example, $50°$ C. to $150°$ C., and conveniently at or about the reflux temperature of the solvent or mixture of solvents used.

Compounds of the formula XIV may be obtained, for example, by heating at reflux a 4-methylphenylboronic acid in a solvent such as methyl chloroform with azeotropic removal of water, followed by radical bromination of the product which may be carried out in situ, for example with bromine and azo(bisisobutyronitrile). The resultant 4-bromomethylphenylboronic acid anhydride may then be used to alkylate a compound of the formula IV (using similar alkylation conditions to those used in process (c) described above), followed by subsequent acidic hydrolysis, to give a formula XIV compound. Alternatively the product from the alkylation step prior to hydrolysis may be isolated and reacted directly with a compound of the formula XV under similar conditions to those described above to obtain a formula XIII compound directly. In a yet further alternative procedure, a 4-methylphenylboronic acid and an appropriate alkanediol, for example 2,2-dimethylpropan-1,3-diol, may be heated at reflux in a solvent (such as cyclohexane) with azeotropic removal of water followed by free radical bromination of the product, which may be carried out in situ. The resultant bromomethyl compound may then be reacted using analogous procedures to those described above for the 4-bromomethylphenylboronic acid anhydride to obtain a formula XIV compound or a compound of the formula XIII directly Compounds of the formula XV may be obtained, for example, as shown in Scheme 4.

Whereafter, an N-oxide or a non-toxic salt or an optically active form of a compound of the formula I may be obtained as described above if desired.

Certain of the intermediates defined herein are novel, for example the compounds of the formula II, III and IX, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The compounds of the invention may also be useful for the treatment of ocular hypertension, glaucoma cognitive disorders (such as Alzheimer's disease, amnesia, senile dementia and learning disorders), as well as other diseases such as renal failure, cardiac insufficiency, post-myocardial infarction, cerebrovascular disorders, anxiety, depression and certain mental illnesses such as schizophrenia.

The antagonism of one or more of the physiological actions of AII and, in particular, the antagonism of the interaction of AII with the receptors which mediate its effects on a target tissue, may be assessed using one or more of the following, routine laboratory procedures:

Test A:

This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the $IC_{50}$ (concentration of for 50% displacement of radiolabelled AII binding), concentrations of the test compound are ordinarily chosen to allow testing over at least four orders of magnitude centred about the predicted approximate $IC_{50}$, which latter is subsequently determined from a plot of percentage displacement against concentration of the test compound.

In general, acidic compounds of formula I as defined above show significant inhibition in Test A at a concentration of 50 micromolar or much less.

Test B:

This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, acidic compounds of formula I as defined above show significant inhibition in Test B at a final concentration of 50 micromolar or much less. [Note: Compounds of formula I wherein Z is a group of the formula —CO.OR$^5$ in which R$^5$ is other than hydrogen in general show only weak activity in the in vitro Tests A or B.]

Test C:

This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D:

This in vivo involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt or N-oxide thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I, or a non-toxic salt thereof, may also be advantageously administered for therapeutic or prophylactic purposes together with another pharmacological agent known in the general art to be of value in treating one or more of the diseases or medical conditions referred to hereinabove, such as a beta-adrenergic blocker (for example atenolol), a calcium channel blocker (for example nifedipine), an angiotensin converting enzyme (ACE) inhibitor (for example lisinopril) or a diuretic (for example furosemide or hydrochlorothiazide). It is to be understood that such combination therapy constitutes a further aspect of the present invention.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18°-26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were normally determined at 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d, doublet;

(vi) $^{13}$C NMR spectra were normally determined at 100 MHz in CDCl$_3$ or d$_6$-dimethylsulphoxide (d$_6$-DMSO) using the solvent signal as internal standard, and are expressed as chemical shifts (delta values) in parts per million relative to TMS; and (vii) all end-products had satisfactory microanalyses.

EXAMPLE 1

Concentrated hydrochloric acid (0.75 ml) was added to a solution of 7,8-dihydro-2-methyl-4-[(2'-(2-triphenylmethyl-2H-tetrazol-5-yl)biphenyl-4-yl)methoxy]-5H-pyrano[4,3-b]pyridine (A1) (0.94 g) in ethanol (6 ml) and methanol (3 ml). The solution was left to stand for 18 hours, and the precipitated solid collected by filtration, and washed with ether to give 7,8-dihydro-2-methyl-4-[(2'-(1H-tetrazol-5-yl)biphenyl-4-yl)methoxy]-5H-pyrano[4,3-b]-pyridine hydrochloride (0.47 g), as a white solid, m.p. 173°–175° C.; NMR (d$_6$-DMSO): 2.7(s,3H), 3.0(t,2H), 3.95(t,2H), 4.7(s,2H), 5.4(s,2H), 7.2(d,2H), 7.4(d,2H), 7.5–7.75 (complex m,5H); $^{13}$C NMR (d$_6$-DMSO): 71.0 (benzylic CH$_2$); mass spectrum (negative fast atom bombardment (-ve FAB), DMSO/-Glycerol (GLY)): 398 (M-H)$^-$; microanalysis, found: C,62.8; H,4.9; N,15.9; H$_2$O, 0.9%; C$_{23}$H$_{21}$N$_5$O$_2$.HCl.0.25H$_2$O requires C,62.7; H,5.1; N,15.9; H$_2$O 1.0%.

The starting material A1 was obtained as follows:

(i) A solution of diketene (3.28 g) and 5,6-dihydro-4-(N-morpholino)-2H-pyran (3.0 g) (obtained as described in *J. Org. Chem.*, 1985, 50, 2608) in dichloromethane (10 ml) was heated under reflux for 6 hours. Volatile material was removed by evaporation and the residue was dissolved in dichloromethane (30 ml). The solution was washed with 2M sodium hydroxide solution (2×15 ml), followed by water (15 ml), and then dried (MgSO$_4$). The solvent was removed by evaporation and the residue purified by flash chromatography, eluting with ethyl acetate, to give 7,8-dihydro-2-methylpyrano-[4,3-b]pyran-4(5H)-one (C1) (1.0 g), as an off-white soid, m.p. 107°–110° C.; NMR: 2.3(s,3H), 2.6–2.7(m,2H), 3.9(t,2H), 4.5(t,2H), 6.1(s,1H).

(ii) Compound C1 (1.0 g) and aqueous ammonia solution (density, 0.91 g/ml; 15 ml) were heated at 120° C. in a sealed tube for 10 hours. Volatile material was removed by evaporation and the residue azeotroped with toluene (2×20 ml). The residue was recrystallised from a mixture of methanol and ethyl acetate to give 2-methyl-1,5,7,8-tetrahydropyrano[4,3-b]-pyridin-4-one (B1) (0.70 g), as an off-white solid, m.p. >285° C.; NMR (d$_6$-DMSO): 2.2(s,3H), 2.45–2.6(m,2H), 3.8(t,2H), 4.3(t,2H), 5.8(s,1H) 11.1(br s, 1H).

(iii) Sodium hydride (60% dispersion in mineral oil, 0.144 g) was added to a stirred suspension of compound B1 (0.59 g) in N,N-dimethylformamide (DMF) (20 ml). The mixture was stirred at 50° C. until evolution of hydrogen ceased and then 5-[2-(4'-bromomethylbiphenylyl)]-2-triphenylmethyl-2H-tetrazole (2.0 g) (obtained as described in European Patent Application, Publication No. 291969) was added. The solution was stirred at 50° C. for 4 hours and then at ambient temperature for 18 hours. The solvent was removed by evaporation and the residue partitioned between ethyl acetate (75 ml) and water (75 ml). The organic layer was separated, washed with water (2×25 ml), followed by saturated sodium chloride solution (25 ml) and dried (MgSO$_4$). The solvent was removed by evaporation and the residue purified by flash chromatography, eluting with ethyl acetate, to give 7,8-dihydro-2-methyl-4-[(2'-(2-triphenylmethyl-2H-tetrazol-5-yl)biphenyl-4-yl)-methoxy]-5H-pyrano[4,3b]pyridine (A1) (1.09 g), as a foam; NMR (d$_6$-DMSO): 2.5(s,3H), 2.8(t,2H), 3.9(t,2H), 4.5(s,2H), 5.1(s,2H), 6.8–6.9(m,6H), 7.1(d,2H), 7.1–7.4 (complex m,12H), 7.5–7.7(m,3H), 7.8(dd,1H).

EXAMPLE 2

Using an analogous procedure to that described in Example 1, but starting from 7,8-dihydro-2-ethyl-4-[(2'-(2-triphenylmethyl-2H-tetrazol-5-yl)biphenyl-4-yl)methoxy]-5H-pyrano[4,3-b]pyridine (A2), there was obtained in 57% yield 7,8-dihydro-2-ethyl 4-[(2'-(1H-tetrazol-5-yl)biphenyl-4-yl)methoxy]-5H-pyrano[4,3-b]pyridine hydrochloride, as a white solid, m.p. 213°–214° C.; NMR (CD$_3$OD): 1.4(t,3H), 2.9(q,2H), 3.0(t,2H), 4.0(t,2H), 4.7(s,2H), 5.45(s,2H), 7.2(dd,2H), 7.4(d,2H), 7.5(s,1H), 7.55–7.75(m,4H); mass spectrum (positive fast atom bombardment (+ve FAB), DMSO/m-nitrobenzyl alcohol (NBA)): 414 (M+H)$^+$; microanalysis found: C,64.2; H.5.4; N,15.3%; C$_{24}$H$_{23}$N$_5$O$_2$.HCl requires C,64.1; H,5.3; N,15.6%.

The starting material A2 was obtained as follows:

(i) A mixture of 5-(1-hydroxypropylidine)-2,2-dimethyl-1,3-dioxane-4,6-dione (19.6 g) (obtained as described in *J. Org. Chem.*, 1979, 44, 3089) and 5,6-dihydro-4-(N-morpholino)-2H-pyran (8.2 g) was heated at 120° C. for 2 hours. Dichloromethane (100 ml) was added and the solution was washed successively with 2M sodium hydroxide solution (50 ml), water (50 ml) and saturated sodium chloride solution (50 ml). The solution was dried (MgSO$_4$) and volatile material was removed by evaporation. The residue was purified by flash chromatography, eluting with a mixture of ethyl acetate and hexane (1:3 v/v) to give 7,8-dihydro-2-ethylpyrano[4,3-b]pyran-4(5H)-one (C2) (2.6 g), as an oil; NMR (CDCl$_3$): 1.2(t,3H), 2.6(q,2H), 2.6–2.7(m,2H), 4.0(t,2H), 4.55(t,2H), 6.1(s,1H).

(ii) Using an analgous procedure to that described in Example 1, part (ii), but starting from compound C2, there was obtained in 56% yield 2-ethyl-1,5,7,8-tetrahydropyrano[4,3-b]pyridin-4-one (B2), m.p. 238°–240° C.; NMR (d$_6$-DMSO): 1.2(t,3H), 2.35–2.7(m,4H), 3.8(t,2H), 4.3(s,2H), 5.8(s,1H), 11.1(s,1H).

(iii) Using an analogous procedure to that described in Example 1, part (iii), but starting from compound B2, there was obtained in 93% yield 7,8-dihydro-2-ethyl-4-[(2'-(2-triphenylmethyl-2H-tetrazol-5-yl)biphenyl-4-yl)methoxy]-5H-pyrano[4,3,b]pyridine, m.p. 172°–173° C.; NMR (d$_6$-DMSO): 1.3(t,3H), 2.75(q,2H), 2.95(t,2H), 4.0(t,2H), 4.7(s,2H), 5.0(s,2H), 6.6(s,1H), 6.85–7.0(m,6H), 7.1–7.55 (complex m,16H), 7.8–7.9(m,1H).

EXAMPLES 3 AND 4

Using an analogous procedure to that described in Example 1, but starting from the appropriate triphenylmethyl tetrazoles of formula III, the following compunds of formula I were obtained:

(Example 3): 1,7-Dimethyl-1,2,3,4-tetrahydro-5-[(2'-(1H-tetrazol-5-yl)biphenyl-4-yl)methoxy]-1,8-naphthyridine hydrochloride, in 58% yield; m.p. 231°–232° C.; NMR (d$_6$-DMSO): 1.8–1.9(m,2H), 2.5(s,3H), 2.5–2.65(m,2H), 3.2(s,3H), 3.35–3.45(m,2H), 5.3(s,2H), 6.8(s,2H), 7.1(d,2H), 7.45(d,2H), 7.55–7.75(m,2H); mass spectrum (-ve FAB, DMSO/GLY): 411 (M-H)$^-$; microanalysis, found: C,64.1; H,5.5; N,18.4; H$_2$O, 1.6%; C$_{24}$H$_{24}$N$_6$O.HCl.0.25H$_2$O requires: C,63.6; H,5.4; N,18.5; H$_2$O 1.0%.

(Example 4): 2,3-Dihydro-1,6-dimethyl-4-[(2'-(1H-tetrazol-5-yl)-biphenyl-4-yl)methoxy]-1H-pyrrolo[2,3-b]pyridine hydrochloride, in 80% yield; m.p. 205°–208° C.; NMR (d$_6$-DMSO): 2.4(s,3H), 3.0(t,2H), 3.15(s,3H), 3.7(t,2H), 5.3(s,2H), 6.6(s,1H), 7.1(d,2H), 7.4(d,2H), 7.5–7.7(m,4H); $^{13}$C NMR (d$_6$-DMSO): 70.0 (benzylic CH$_2$); mass spectrum (-ve FAB DMSO/NBA): 397 (M-H)$^-$; microanalysis, found: C,62.8; H,5.4; N,18.1; H$_2$O, 0.8%; C$_{23}$H$_{22}$N$_6$O.HCl.0.25H$_2$O.0.2 Dioxan requires: C,62.5; H,5.2; N,18.4; H$_2$O, 1.0%

The necessary starting materials of formula III used in Examples 3 and 4 (corresponding to starting material A1 in Example 1), were obtained using an analogous procedure to that described in Example 1, part (iii), as follows:

(Example 3A): 1,7-Dimethyl-1,2,3,4-tetrahydro-5-[(2'-(2-triphenylmethyl-2H-tetrazol-5-yl)biphenyl-4-yl)methoxy]-1,8-naphthyridine, isolated as a foam in 60% yield; NMR: 1.8-1.9(m,2H), 2.4(s,3H), 2.6-2.7(m,2H), 3.2(s,3H), 3.2-3.3(m,2H), 4.95(s,2H), 6.1(s,1H), 6.8-7.0(m,6H), 7.1-7.55 (complex m,16H), 7.9-8.0(m,1H); starting from 1,7-dimethyl-1,2,3,4-tetrahydro-1,8-naphthyridin-5(8H)-one, itself obtained as described in *Chemistry of Heterocyclic Compounds,* 1976, 672.

(Example 4A): 2,3 Dihydro-1,6-dimethyl-4-[(2'-(2-triphenylmethyl-2H-tetrazol-5-yl)biphenyl-4-yl)methoxy]-1H-pyrrolo[2,3-b]pyridine, as a foam in 24% yield; NMR: 2.4(s,3H), 2.8-2.9(m,2H), 3.0(s,3H), 3.4-3.5(m,2H), 5.0(s,2H), 6.1(s,1H), 6.8-7.0(m,9H), 7.1-7.6 (complex m,13H), 7.9-8.0(m,1H); starting from 1,6-dimethyl-1,2,3,7-tetrahydropyrrolo[2,3-b]pyridin-4-one, itself obtained as described in *Chemistry of Heterocyclic Compounds,* 1976, 672.

EXAMPLE 5

Using an analogous procedure to that described in Example 1, but starting from 2-ethyl-5,6,7,8-tetrahydro-4-[(2'-(2-triphenylmethyl-2H-tetrazol-5-yl)biphenyl-4-yl)methoxy]-1,5-naphthyridine (A5), there was obtained in 63% yield 2-ethyl-5,6,7,8-tetrahydro-4-[(2'-(1H-tetrazol-5-yl)biphenyl-4-yl)methoxy]-1,5-naphthyridine hydrochloride, as a white powder, m.p. 219°-220° C.; NMR (d$_6$-DMSO): 1.3(t,3H), 1.8-2.0(m,2H), 2.85(q,2H), 3.0(t,2H), 3.2-3.3(m,2H), 5.4(s,2H), 5.8-6.2(br s, 1H), 7.2(d,1H), 7.3(s,1H), 7.4-7.75 (complex m,6H); mass spectrum (+ve FAB, DMSO/NBA): 413 (M+H)$^+$; microanalysis, found: C,60.6; H,5.4; N,17.5; Cl, 7.6%; $C_{24}H_{24}N_6O \cdot HCl \cdot 1.5 H_2O$ requires: C,60.6; H,5.9; N,17.7; Cl, 7.5%.

The starting material A5 was obtained as follows:

(i) A solution of 5-amino-2-methoxypyridine (50 g), methyl propionylacetate (57.3 g) and p-toluenesulphonic acid (0.5 g) in benzene (200 ml) was heated under reflux with azeotropic removal of water for 20 hours. Volatile material was removed by evaporation and the residue added to a refluxing eutectic mixure of 26.5% v/v diphenyl and 73.5% v/v diphenyl oxide (140 ml). The solution was heated under reflux for 1 hour, cooled and diluted with hexane (500 ml). The precipitated solid was filtered off and triturated with hot methanol (500 ml) to give 2-ethyl-6-methoxy-1,5-naphthyridin-4(1H)-one (E5) (32.3 g), as a pale brown solid, m.p. 279°-281° C.; NMR (d$_6$-DMSO): 1.2(t,3H), 2.65(q,2H), 3.95(s,3H), 6.3(br s, 1H), 7.15(d,1H), 7.95(d,1H).

(ii) Compound E5 (5.0 g) was dissolved in glacial acetic acid (50 ml) and catalytically hydrogenated at atmospheric pressure over platinum oxide (0.5 g). When hydrogen uptake ceased, the catalyst was removed by filtration through diatomaceous earth. The solvent was removed by evaporation and the residue purified by flash chromatography eluting with ethyl acetate/methanol/aqueous ammonia (17:2:1 v/v), to give 2-ethyl-5,6,7,8-tetrahydro-1,5-naphthyridin-4(1H)-one (D5) (3.2 g), m.p. 206°-209° C. (after trituration with ethyl acetate); NMR (d$_6$-DMSO): 1.15(t,3H), 1.7-1.9(m,2H), 2.35(q,2H), 2.55(t,2H), 3.1(t,2H), 5.75(s,1H), 10.6-11.1(br s,1H).

(iii) Trifluoroacetic anhydride (1.73 g) was added to a stirred solution of compound D5 (1.35 g) and triethylamine (0.76 g) in dichloromethane (150 ml) at 0° C. under an atmosphere of argon. The solution was allowed to warm to ambient temperature and volatile material was removed by evaporation. The residue was triturated with ethyl acetate to give 2-ethyl-5,6,7,8-tetrahydro-5-trifluoroacetyl-1,5-naphthyridin-4-(1H)-one (C5) (1.62 g), m.p. 271°-274° C.; NMR (d$_6$-DMSO+d$_4$-acetic acid): 1.2(t,3H), 1.9-2.1(m,2H), 2.6(q,2H), 2.8(t,2H), 3.5-3.8(m,2H), 6.3(s,1H); mass spectrum (+ve chemical ionisation (CI), NH$_3$): 275 (M+H)$^+$.

(iv) Using an analogous procedure to that described in Example 1, part (iii), but starting from compound C5, there was obtained in 40% yield 2-ethyl-5,6,7,8-tetrahydro 5-trifluoroacetyl-4-[(2'-(2-triphenylmethyl-2H-tetrazol-5-yl)biphenyl-4-yl)methoxy]-1,5-naphthyridine (B5), m.p. 93°-95° C.; NMR (d$_6$-DMSO): 1.25(t,3H), 1.9-2.2(m,2H), 2.7(q,2H), 2.8-2.9(m,2H), 3.5-3.9(m,2H), 5.15(dd,2H), 6.8-6.9(m,6H), 6.95(s,1H), 7.1(d,2H), 7.2-7.75(complex m,14H), 7.8(dd,1H).

(v) A solution of compound B5 (0.42 g) and potassium hydroxide (0.1 g) in methanol (5 ml) was left to stand for 1 hour. The solvent was removed by evaporation and the residue partitioned between ethyl acetate (20 ml) and water (20 ml). The organic phase was separated, washed with saturated sodium chloride solution (20 ml) and dried (MgSO$_4$) The solvent was removed by evaporation and ether (10 ml) was added to the residue. Insoluble material was removed by filtration and the filtrate was evaporated to give 2-ethyl 5,6,7,8-tetrahydro-4-(2'- 2-triphenylmethyl-2H-tetrazol-5-yl)biphenyl)-4-yl)methoxy]-1,5-naphthyridine (A5) (0.12 g), as a foam; NMR (d$_6$-DMSO): 1.15(t,3H), 1.8-1.9(m,2H), 2.5(q,2H), 2.7(t,2H), 3.05-3.15(m,2H), 5.05(s,2H), 6.65(s,1H), 6.8-6.9(m,6H), 7.1(d,2H), 7.2-7.7(complex m,14H), 7.9(dd,1H).

EXAMPLE 6

Using an analogous procedure to that described in Example 1, but starting from 2-ethyl-5,6,7,8-tetrahydro-4-[(2'-(2 -triphenylmethyl-2H-tetrazol-5-yl)biphenyl-4-yl)methoxy]-1,6-naphthyridine (A6), there was obtained in 69% yield 2-ethyl-5,6,7,8-tetrahydro-4-[(2'-(1H-tetrazol-5-yl)biphenyl-4-yl)methoxy]-1,6-naphthyridine dihydrochloride, as a foam; NMR (d$_6$-DMSO, d$_4$-acetic acid): 1.4(t,3H), 3.05(q,2H), 3.3-3.7(m,4H), 4.3(s,2H), 5.55(s,2H), 7.1-7.9(complex m,9H); mass spectrum (+ve FAB, DMSO/NBA): 413 (M+H)$^+$.

The starting material A6 was obtained as follows:

(i) A solution of 1-benzyl-4-(N-morpholino)-1,2,5,6-tetrahydropyridine (9.32 g) (obtained as described in *J. Heterocyclic Chem.,* 1975, 12, 809) and methyl propionylacetate (10.4 g) in xylene (20 ml) was heated under reflux with azeotropic removal of water for 24 hours. The solution was added to 1M sulphuric acid (100 ml) and the mixture was extracted with dichloromethane (3×100 ml). The aqueous phase was basified by addition of solid sodium hydroxide pellets and the resulting emulsion was extracted with dichloromethane (3×100 ml). The extracts were washed with water (100 ml), followed by saturated sodium chloride solution (100 ml), and then dried (MgSO$_4$). Volatile material was removed by evaporation and the residue purified by flash chromatography eluting with ethyl acetate, to give 6-benzyl-2-ethyl-5,6,7,8-tetrahydro-4H-pyrano[3,2-c]pyridin-4-one (F6) (1.72 g), as an oil; NMR: 1.2(t,3H), 2.5(q,2H), 2.6–2.8(m,4H), 3.4(t,2H), 3.7(s,2H), 6.1(s,1H), 7.2–7.4(m,5H).

(ii) A solution of compound F6 (1.72 g) in benzylamine (10 ml) was heated under reflux for 24 hours. Volatile material was removed by evaporation and the residue dissolved in ethyl acetate (100 ml). The solution was washed with water (20 ml) and dried (MgSO4). The solvent was removed by evaporation and the residue purified by flash chromatography, eluting with methanol/ethyl acetate on a gradient from 0 to 20% v/v, to give 1,6-dibenzyl-2-ethyl-5,6,7,8-tetrahydro-1,5-naphthyridin-4(1H)-one (E6) (1.08 g), as an oil; NMR: 1.2(t,3H), 2.5–2.7(m,6H), 3.6(s,2H), 3.7(s,2H), 5.1(s,2H), 6.3(s,1H), 6.9(d,2H), 7.2–7.4(m,8H).

(iii) A solution of compound E6 (2 2 g) in methanol (30 ml) containing concentrated hydrochloric acid (1.4 ml) was catalytically hydrogenated at atmospheric pressure over 10% palladium on charcoal (0.22 g). When hydrogen uptake ceased, the catalyst was removed by filtration through diatomaceous earth. The solvent was removed by evaporation and the residue triturated with a mixture of methanol and ethyl acetate (1:1 v/v) to give 2-ethyl-5,6,7,8-tetrahydro-1,6-naphthyridin-4(1H)-one dihydrochloride (D6) (1.4 g), as a white solid, m.p. >300° C.; NMR (d6-DMSO): 1.3(t,3H), 2.9(q,2H), 3.3(t,2H), 3.45(t,2H), 4.1(s,2H), 7.1(s,1H), 9.8–10.2 (br s,2H).

(iv) Trifluoroacetic anhydride (8.3 g) was added dropwise over a period of 5 minutes to a stirred solution of compound D6 (1.0 g) and triethylamine (0.79 g) in pyridine (13 ml) under an atmosphere of argon. Volatile material was removed by evaporation and water (100 ml) was added to the residue. The mixture was extracted with ethyl acetate (3×200 ml) and the extracts were washed with saturated sodium chloride solution (100 ml) and dried (MgSO4). The solvent was removed by evaporation and the residue triturated with ether to give 2-ethyl-5,6,7,8-tetrahydro-6-trifluoroacetyl-1,6-naphthyridin-4(1H)-one (C6) (1.0 g), as a white solid, m.p. >300° C.; NMR (d6-DMSO): 1.2(t,3H), 2.5(q,2H), 2.8(q,2H), 3.7(q,2H), 4.35(d,2H), 5.9(s,1H), 11.2(br s, 1H).

(v) Potassium carbonate (0.54 g) was added to a solution of compound C6 (1.07 g) and 5-[2-(4'-bromomethylbiphenylyl)]2-triphenylmethyl-2H-tetrazole (2.35 g) in DMF (20 ml). The mixture was stirred for 72 hours and then added to water (200 ml). The precipitated solid was filtered off and purified by flash chromatography, eluting with ethyl acetate/hexane on a gradient from 1:1 v/v to 7:3 v/v, to give 2-ethyl-5,6,7,8-tetrahydro-6-trifluroroacetyl-4-[(2'-(2-triphenylmethyl-2H-tetrazol-5-yl)biphenyl-4-yl)methoxy]-1,6-naphthyridine (B6) (1.34 g), as a foam; NMR (d6-DMSO): 1.3(t,3H), 2.65(q,2H), 2.9(q,2H), 3.9(q,2H), 4.6(d,2H), 5.2(d,2H), 6.8–7.8 (complex m,24H).

(vi) A mixture of compound B6 (1.34 g), potassium carbonate (0.45 g), ether (13 ml), methanol (9 ml) and water (7.8 ml) was stirred for 16 hours. Ethyl acetate (100 ml) and water (20 ml) were added. The organic phase was separated, washed with saturated sodium chloride solution (20 ml) and dried (MgSO4). Volatile material was removed by evaporation to give 2-ethyl-5,6,7,8-tetrahydro-4-[(2'-(2-triphenylmethyl-2H-tetrazol-5-yl)biphenyl-4-yl)methoxy]-1,6-naphthyridine (A6) 1.02 g), as a foam; NMR (d6-DMSO): 1.2(t,3H), 2.55–2.75(m,4H), 3.0(t,2H), 3.7(s,2H), 5.1(s,2H), 6.7–6.9(m,7H), 7.1(d,2H), 7.2–7.7 (complex m,14H), 7.8(dd,1H).

EXAMPLE 7

Using an analogous procedure to that described in Example 1, but starting from 2-ethyl-6-methyl-5,6,7,8-tetrahydro-4-[(2'-(2-triphenylmethyl-2H-tetrazol-5-yl)biphenyl-4-yl)methoxy]-1,6-naphthyridine, there was obtained in 71% yield 2-ethyl-6-methyl-5,6,7,8-tetrahydro-4-[(2'-(1H-tetrazol-5-yl)biphenyl-4-yl)methoxy]-1,6-naphthyridine hydrochloride, as a white solid, m.p. 224°–227° C.; NMR (d6 DMSO, d4-acetic acid): 1.4(t,3H), 3.0(q,2H), 3.1(s,3H), 3.45(t,2H), 3.7(q,2H), 4.4(s,2H), 5,5(s,2H), 7.2(d,2H), 7.4–7.8 (complex m,7H); mass spectrum (+ve FAB, DMSO/NBA): 427 (M+H)+.

A The starting material was obtained as follows:

A solution of 2-ethyl-5,6,7,8-tetrahydro-4-[(2'-(2-triphenylmethyl-2H-tetrazol-5-yl)biphenyl-4-yl)methoxy]-1,6-naphthyridine (500 mg) in dry tetrahydrofuran (THF) (2 ml) was added dropwise over a period of 20 minutes to a stirred suspension of lithium aluminium hydride (116 mg) in dry THF (2 ml) under an atmosphere of argon. The mixture was cooled to 0° C. and ethyl formate (173 mg) was added dropwise over a period of 10 minutes. The mixture was stirred for 1 hour and then water (0.12 ml), 4M sodium hydroxide solution (0.12 ml) and water (0.36 ml) were added successively. Stirring was continued for 10 minutes, and then insoluble material was removed by filtration and washed with ether (50 ml). The combined filtrate and washings were evaporated to dryness and the residue purified by flash chromatography, eluting with a mixture of methanol and dichloromethane (1:9 v/v). to give 2-ethyl-6-methyl-5,6,7,8-tetrahydro-4-[(2'-(2-triphenylmethyl-2H-tetrazol-5-yl)biphenyl-4-yl)-methoxy]-1,6-naphthyridine (240 mg), as a pale yellow solid, m.p. 143°–144° C.; NMR (d6-DMSO, d4-acetic acid): 1.2(t,3H), 2.65(q,2H), 2.95(s,4H), 3.65(s,2H), 5.15(s,2H), 6.8–6.9(m,7H), 7.1(d,2H), 7.3–7.7 (complex m,14H), 7.85(dd,1H).

EXAMPLE 8

Using an analogous procedure to that described in Example 1, but starting from 6-acetyl-2-ethyl-5,6,7,8-tetrahydro-4-[(2'-(2-triphenylmethyl-2H-tetrazol-5-yl)biphenyl-4-yl)methoxy]-1,6-naphthyridine there was obtained in 75% yield 6-acetyl-2-ethyl-5,6,7,8-tetrahydro-4-[(2'-(1H-tetrazol-5-yl)biphenyl-4-yl)methoxy]-1,6-naphthyridine hydrochloride, as a pale yellow solid, m.p. 170°–190° C. (decomp); NMR (d6-DMSO, d4-acetic acid): 1.4(t,3H), 2.2(s,3H), 3.0–3.3(m,4H), 3.8(s,2H), 4.6(s,2H), 5.5(s,2H), 7.2(d,2H), 7.4–7.8 (complex m,7H); mass spectrum (+ve FAB, DMSO/NBA): 455 (M+H)+.

The starting material was obtained as follows:

Acetic anhydride (78 mg) was added to a stirred solution of 2-ethyl-5,6,7,8-tetrahydro-4-[(2'-(2-triphenylmethyl-2H-tetrazol-5-yl) biphenyl-4-yl)methoxy]-1,6-naphthyridine (500 mg) and triethylamine (150 mg) in dichloromethane (10 ml) under an atmosphere of argon. The solution was left to stand for 20 hours and then volatile material was removed by evaporation. The residue was purified by flash chromatography, eluting with a mixture of methanol/ethyl acetate (1:9 v/v), to give 6-acetyl-2-ethyl-5,6,7,8-tetrahydro-4-[(2'-(2-triphenylmethyl-2H-tetrazol-5-yl)biphenyl-4-yl)methoxy]-1,6-naphthyridine (350 mg), m.p. 97°–98° C.; NMR ($d_6$-DMSO, $d_4$-acetic acid): 1.25(t,3H), 2.15(s,3H), 2.75(q,2H), 2.9–3.0(m,3H), 3.7(m,2H), 4.5(d,2H), 5.2(s,2H), 6.8–7.7 (complex m,23H), 7.75–7.85(m,1H).

EXAMPLE 9

Using an analogous procedure to that described in Example 1, but starting from 6-benzyl-2-ethyl-5,6,7,8-tetrahydro-4-[(2'-(2-triphenymethyl-2H-tetrazol-5-yl)biphenyl-4-yl)methoxy]-1,6-naphthyridine (A9), there was obtained in 25% yield 6-benzyl-2-ethyl-5,6,7,8-tetrahydro-4-[(2'-(1H-tetrazol-5-yl)biphenyl-4-yl)methoxy]-1,6-naphthyridine dihydrochloride, as a white solid, m.p. 203°–204° C.; NMR ($d_6$-DMSO, $d_4$-acetic acid): 1.4(t,3H), 3.0(q,2H), 3.4–3.5(m,2H), 3.6–3.7(m,2H), 4.25(s,2H). 4.55(s,2H), 5.5(s,2H), 7.2(d,2H), 7.35(d,2H), 7.5–7.7(complex m,10H); mass spectrum (+ve FAB, DMSO/NBA): 503 $(M+H)^+$; microanalysis, found: C,64.0; H,5.8; N,14.4; Cl,12.2.; $H_2O$, 2.2%; $C_{26}H_{26}N_6O_2.2HCl.0.6\ H_2O$ requires: C,63.5; H,5.7; N,14.3; Cl, 12.1; $H_2O$, 1.8%.

The starting material A9 was obtained as follows:

(i) Using an analogous procedure to that described in Example 1, part (ii), but starting from 6-benzyl-2-ethyl-5,6,7,8-tetrahydro-4H-pyrano[3,2-c]pyridin-4-one, there was obtained in 13% yield 6-benzyl-2-ethyl-5,6,7,8-tetrahydro-1,6-naphyridin-4(1H)-one (B9), m.p. 224°–225° C.; NMR ($d_6$-DMSO, $d_4$-acetic acid): 1.0(t,3H), 2.3(q,2H), 2.6(t,2H), 2.75(t,2H), 3.25(s,2H), 3.7(s,2H), 5.95(s,1H), 7.15–7.25(m,5H).

(ii) Using an analogous procedure to that described in Example 1, part (iii), but starting from compound B9, there was obtained in 32% yield 6-benzyl-2-ethyl-5,6,7,8-tetrahydro-4-[2'-(2-triphenylmethyl-2H-tetrazol-5-yl)biphenyl-4-yl)methoxy]-1,6-naphthyridine (A9), m.p. 150°–153° C. (decomp.); NMR ($d_6$-DMSO): 1.2(t,3H), 2.5–2.9(m,6H), 3.4(s,2H), 3.6(s,2H), 5.1(s,2H), 6.8–6.9(m,7H), 7.1(d,2H), 7.2–7.7 (complex m,19H), 7.8(dd,1H).

EXAMPLE 10

Using an analogous procedure to that described in Example 1, but starting from 5,6-dihydro-2-ethyl-4-[(2'-(2-triphenylmethyl-2H-tetrazol-5-yl)biphenyl-4-yl)methoxy]-8H-pyrano[3,4-b]pyridine (A10), there was obtained in 71% yield 5,6-dihydro-2-ethyl-4-[(2'-(1H-tetrazol-5-yl)biphenyl-4-yl)methoxy]-8H-pyrano[3,4-b]pyridine hydrochloride, as a white solid, m.p. 216°–218° C.; NMR ($d_6$-DMSO): 1.35(t,3H), 2.7(t,2H), 2.95(q.2H), 3.9(t,2H), 4.9(s,2H), 5.5(S,2H), 7.2(dd,2H), 7.4–7.75 (complex m,7H); mass spectrum (+ve FAB, DMSO/NBA): 414 $(M+H)^+$; microanalysis, found: C,63.9; H,5.3; N,15.5%. $C_{24}H_{23}N_5O_2.HCl$ requires: C,64.1; H,5.4; N,15.6%.

The starting material A10 was obtained as follows:

(i) Using an analogous procedure to that described in Example 2, part (i), but starting from 5,6-dihydro-3-(N-morpholino)-4H-pyran (obtained as described in *Arch. Pharm.* 1984, 317, 958) there was obtained in 12% yield 5,6-dihydro-2-ethylpyrano[3,4-b]pyran-4(8H)-one (C10), as an oil; NMR ($CDCl_3$): 1.2(t,3H), 2.45–2.7(m,4H), 3.9(t,2H), 4.4(t,2H), 6.1(s,1H).

(ii) Using an analogous procedure to that described in Example 1, part (ii), but starting from compound (C10) there was obtained in 67% yield 2-ethyl-1,5,6,8-tetrahydropyrano[3,4-b]pyridin-4-one, m.p. 216°–218° C.; NMR ($d_6$-DMSO): 1.2(t,3H), 2.5–2.75(m,4H), 3.9(t,2H), 4.6(s,2H), 6.5(s,1H), 11.0(br s, 1H); 8% nuclear overhauser enhancement seen between signals at 3.9 delta and 11.0 delta.

(iii) Using an analogous procedure to that described in Example 1, part (iii), but starting from compound B10, there was obtained in 68% yield, 5,6-dihydro-2-ethyl-4-[(2'-(2-triphenylmethyl-2H-tetrazol-5-yl)biphenyl-4-yl)methoxy]-8H-pyrano[3,4-b]pyridine, m.p. 168°–170° C.; NMR ($CDCl_3$): 1.3(t,3H), 2.7(q,2H), 3.9(t,2H), 4.7(s,2H), 5.0(s,2H), 6.6(s,1H), 6.7–6.95(m,6H), 7.2–7.55 (complex m,16H), 7.9–8.0(m,1H).

EXAMPLE 11

Using an analogous procedure to that described in Example 1, but starting from 7,8-dihydro-2-ethyl-4-[(2'-(2-triphenylmethyl-2H-tetrazol-5-yl)biphenyl-4-yl)methoxy]-5H-thiopyrano[4,3-b]pyridine (A), there was thus obtained in 44% yield 7,8-dihydro-2-ethyl-4-[(2'-(1H-tetrazol-5-yl)biphenyl-4-yl)methoxy]-5H-thiopyrano[4,3-b]pyridine hydrochloride, m.p. 215°–217° C.; NMR ($d_6$-DMSO): 1.3(t, 3H), 2.9–3.1(m, 4H), 3.3(t, 2H), 3.8(s, 2H), 5.5(s, 2H), 7.2 (d, 2H), 7.45–7.7(m, 7H); microanalysis, found: C, 61.3; H, 5.1; N, 15.0; $H_2O$, 0.7%; $C_{24}H_{23}N_5OS.HCl.0.25H_2O$ requires: C, 61.3; H, 5.2; N, 14.9; $H_2$, 1.0%.

The starting material (A) was obtained as follows:

(i) A solution of tetrahydrothiopyran-4-one (20.0 g), morpholine (15.0 g) and p-toluenesulphonic acid (200 mg) in toluene (100 ml) was heated under reflux for 24 hours with azeotropic removal of water. Volatile material was removed by evaporation and the residue was heated with 5-(1-hydroxypropylidene)-2,2-dimethyl-1,3-dioxane-4,6-dione (68 g) at 120° C. for 3 hours. The mixture was dissolved in dichloromethane (300 ml) and the solution was washed with 2M sodium hydroxide solution (2×100 ml), water (2×100 ml) and saturated sodium chloride solution (100 ml). The organic phase was then dried ($MgSO_4$) and volatile material was removed by evaporation. The residue was purified by flash chromatography, eluting with ethyl acetate/hexane (1:1 v/v), to give 7,8-dihydro-2-ethyl-thiopyrano[4,3-b]pyran-4(5H)-one (B) (9.2 g), as an oil; NMR ($CDCl_3$) 1.2(t, 3H). 2.55(q, 2H), 2.8–2.9(m, 4H), 3.55(s, 2H), 6.1(s, 1H).

(ii) Using an analogous procedure to that described in Example 1, part (ii), but starting from compound B, there was obtained in 33% yield 2-ethyl-1,5,7,8-tetrahydrothiopyrano[4,3-b]pyridin-4-one (C), as a semi-solid; NMR ($CDCl_3$) 1.2(t, 3H), 2.6(q, 2H), 2.8(t, 2H), 3.05(t, 2H), 3.6(s, 2H), 4.6–5.6(br, 1H), 6.2(s, 1H).

(iii) Using an analogous procedure to that described in Example 1, part (iii), but starting from compound C, there was obtained in 42% yield, 7,8-dihydro-2-ethyl-4-[(2'-(2-triphenylmethyl-2H-tetrazol-5-yl)biphenyl-4-yl)methoxy]-5H-thiopyrano[4,3-b]pyridine (A), as a foam; NMR ($CDCl_3$): 1.3(t, 3H), 2.75(q, 2H), 2.9(t, 2H), 3.2(t, 2H), 3.7(s, 2H), 5.0(s, 2H), 6.6(s, 1H), 6.7–6.9(m, 6H), 7.1–7.3(m, 16H), 7.45–7.5(m, 1H).

EXAMPLE 12

Using an analogous procedure to that described in Example 1, but starting from 7,8-dihydro-2-ethyl-4-[(2'-(2-triphenylmethyl-2H-5 tetrazol-5-yl)biphenyl-4-yl)methoxy]-5H-thiopyrano[4,3-b]pyridine S-oxide (A) there was obtained in 50% yield 7,8-dihydro-2-ethyl-4-[(2'-(1H-tetrazol-5-yl)biphenyl-4-yl)methoxy]-5H-thiopyrano[4,3-b]-pyridine S-oxide hydrochloride, m.p.

164°–168° C.; NMR (d6-DMSO): 1.3(t, 3H), 2.85–3.2(m, 4H), 3.3–3.6(m, 2H), 4.0(dd, 2H), 5.5(s, 2H), 7.15(d, 2H), 7.45–7.7(m, 7H); mass spectrum (+ve FAB, DMSO/NBA): 446 (M+H)+; microanalysis, found: C, 56.8; H, 5.4; N, 13.4; H2O, 5.1%; $C_{24}H_{23}N_5O_2S \cdot HCl \cdot 1.5H_2O$ requires; C, 56.6; H, 5.3; N, 13.8; H2O, 5.3%.

The starting material (A) was obtained as follows:

A solution of 7,8-dihydro-2-ethyl-4-[(2'-(2-triphenylmethyl-2H-tetrazol-5-yl)biphenyl-4-ylmethoxy]-5H-thiopyrano[4,3-b]-pyridine (500 mg) in dichloromethane (4 ml) was added to a 0.5M solution of sodium metaperiodate in water (1.64 ml) at 0° C. Benzyltriethylammonium chloride (50 mg) was added and the mixture was stirred at 0° C. for 6 hours and at ambient temperature for 16 hours. The mixture was diluted with water (15 ml) and dichloromethane (15 ml). The organic layer was separated and dried (MgSO4). The solvent was removed by evaporation and the residue was purified by flash chromatography, eluting with methanol/dichloromethane (1:49 v/v), to give 7,8-dihydro-2-ethyl-4-[(2'-(2-triphenylmethyl-2H-tetrazol-5-yl)biphenyl-4-yl)methoxy]-5H-thiopyrano[4,3-b]pyridine S-oxide (A) (180 mg), as a foam; NMR (CDCl3) 1.3(t, 3H), 2.8–3.0(m, 4H), 3.25–3.5(m, 2H), 3.85(dd, 2H), 5.0(s, 2H), 6.7(s, 1H), 6.9–7.0(m, 6H), 7.15–7.6(m, 16H), 7.9–8.0(m, 1H).

EXAMPLE 13

Using an analogous procedure to that described in Example 1, but starting from 7,8-dihydro-2-ethyl-4-[(2'-(2-triphenylmethyl-2H-tetrazol-5-yl)biphenyl-4-yl)methoxy]-5H-thiopyrano[4,3-b]pyridine S,S-dioxide (A), there was thus obtained in 61% yield 7,8-dihydro-2-ethyl-4-[(2'-(1H-tetrazol-5-yl)biphenyl-4-yl)methoxy]-5H-thiopyrano[4,3-b]pyridine S,S-dioxide hydrochloride, m.p. 229°–231° C.; NMR (d6-DMSO): 1.3(t, 3H), 3.0(q, 2H), 3.3–3.7(m, 4H), 4.4(s, 2H), 5.5(s, 2H), 7.15(d, 2H), 7.45–7.7(m, 7H); mass spectrum (+ve FAB, DMSO/Methanol/NBA): 462 (M+H)+; microanalysis, found: C, 57.6; H, 4.9; N, 13.9%; $C_{24}H_{23}N_5O_3S \cdot HCl$ requires: C, 57.9; H, 4.9; N, 14.1%.

The starting material (A) was obtained as follows:

Monoperoxyphthalic acid, magnesium salt hexahydrate (1.38 g) was added to a mixture of 7,8-dihydro-2-ethyl-4-[(2'-(2-triphenylmethyl-2H-tetrazol-5-yl)biphenyl-4-yl)methoxy]-5H-thiopyrano[4,3-b]pyridine (1.5 g) and benzyltriethylammonium chloride (0.3 g) in dichloromethane (50 ml) and water (20 ml). The mixture was stirred for 4 hours and then a further quantity of monoperoxyphthalic acid, magnesium salt hexahydrate (138 mg) was added. Stirring was continued for 1 hour and then the mixture was diluted with dichloromethane (100 ml) and water (100 ml). The organic layer was separated and dried (MgSO4) and the solvent was removed by evaporation. The residue was purified by flash chromtography, eluting with methanol/dichlormethane (1.49 v/v) to give 7,8-dihydro-2-ethyl-4-[(2'-triphenylmethyl-2H-tetrazol-5-yl)biphenyl-4yl)methoxy]-5H-thiopyrano[4,3b]pyridine S,S-dioxide (A) (320 mg), as a foam; NMR (CDCl3); 1.3(t, 3H), 2,75(q, 2H), 3.35(t, 2H), 3.55(t, 2H), 4.15(s, 2H), 5.0(s, 2H), 6.65(s, 1H), 6.9–7.0(m, 6H), 7.1–7.5(m, 16H), 7.95–8.0(m, 1H).

EXAMPLE 14

(Note: all parts by weight)

The components of the invention may be administered for therapeutic or prophylactic use to warmblooded animals such as man in the form of conventional pharmaceutical compositions, typical examples of which include the following:

| (a) Capsule (for oral administration) | |
|---|---|
| Active ingredient* | 20 |
| Lactose powder | 578.5 |
| Magnesium stearate | 1.5 |
| (b) Tablet (for oral administration) | |
| Active ingredient* | 50 |
| Microcrystalline cellulose | 400 |
| Starch (pregelatinised) | 47.5 |
| Magnesium stearate | 2.5 |
| (c) Injectable Solution (for intravenous administration) | |
| Active ingredient* | 0.05–1.0 |
| Propylene glycol | 5.0 |
| Polyethylene glycol (300) | 3.0–5.0 |
| Purified water | to 100% |
| (d) Injectable Suspension (for intramuscular administration) | |
| Active ingredient* | 0.05–1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Chemical Formulae

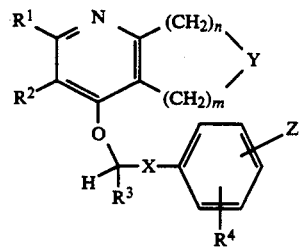

I

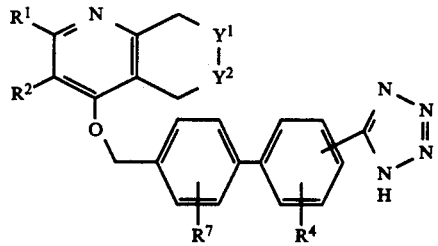

Ia

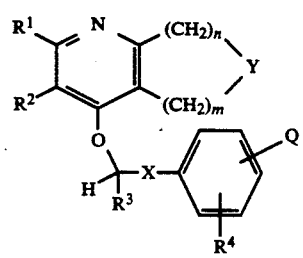

II

-continued

Chemical Formulae

III–XV (chemical structures)

Scheme 1
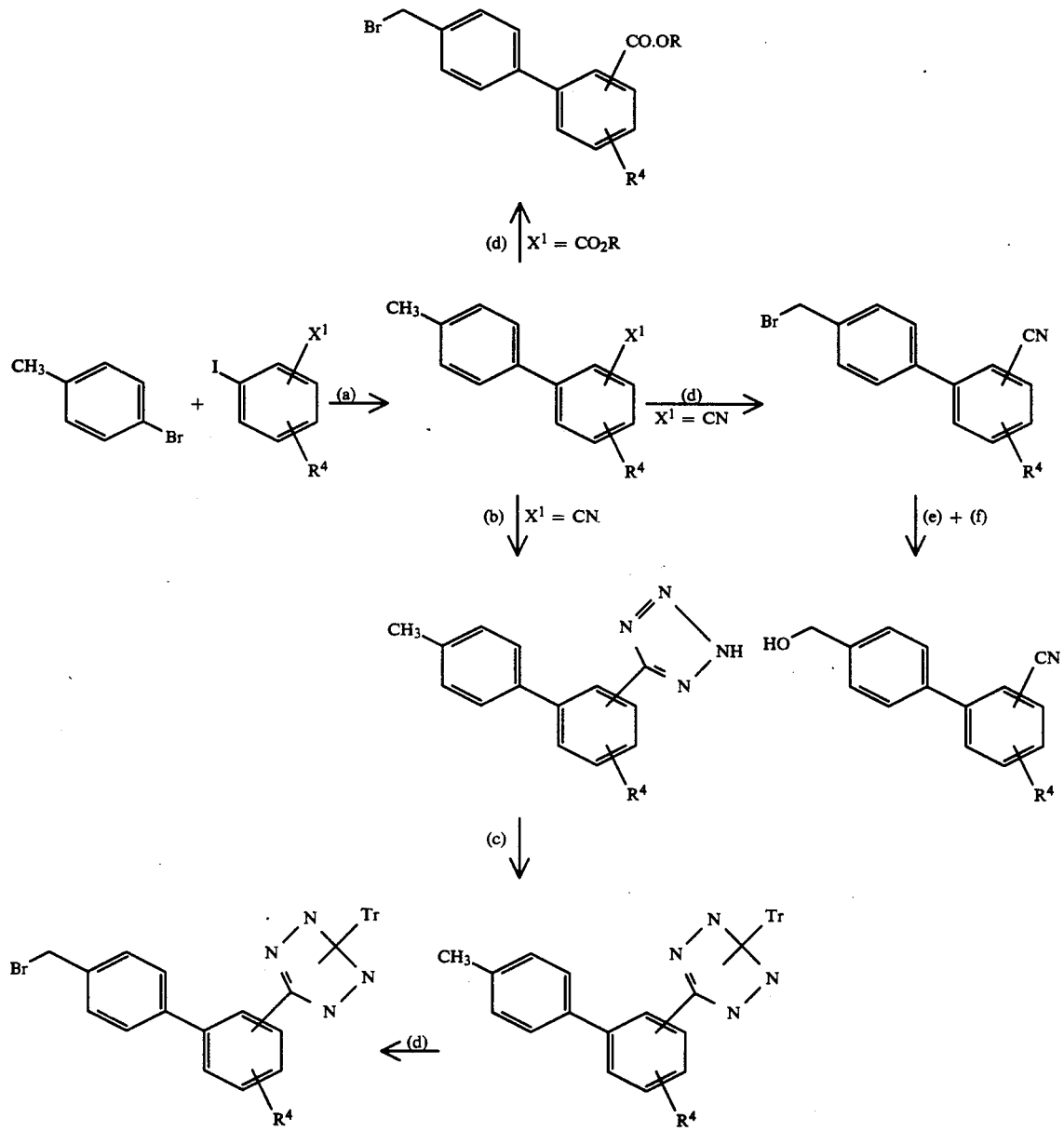
Note:
R = lower alkyl, benzyl, phenyl;
Tr = triphenylmethyl (trityl)
Reagents:
(a) BuLi/THF; $ZnCl_2/Et_2O$; $Pd(Ph_3P)_4$
(b) $Bu_3Sn.N_3$/toluene; HCl/toluene
(c) Tr.Cl/$Et_3N$/$CH_2Cl_2$
(d) N-bromosuccinimide/azoisobutyronitrile/$CCl_4$
(e) Potassium acetate, hexaoxacyclooctadecane, DME, reflux
(f) Lithium borohydride, THF, 0–25° C.

Scheme 2
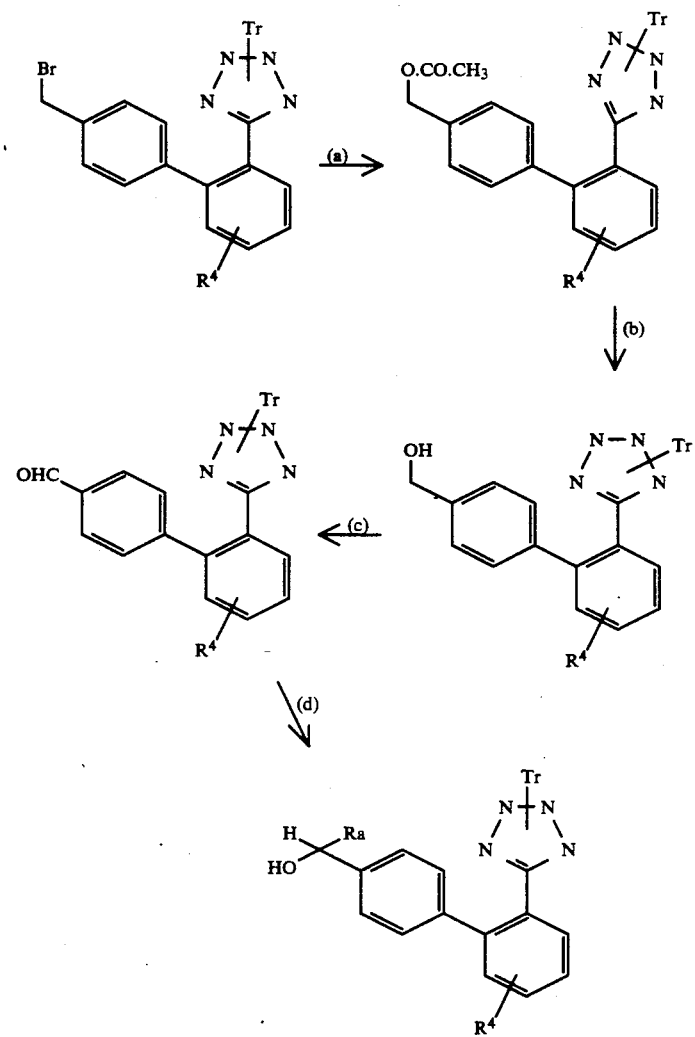
Note:
Tr = triphenylmethyl (trityl);
Ra = (1-4C)alkyl
Reagents:
(a) Potassium acetate, hexaoxacyclooctadecane, DME, reflux
(b) Lithium borohydride, THF, 0-25° C.
(c) Pyridine-SO$_3$ complex, Et$_3$N, DMSO, ambient temperature
(d) Ra.M, Et$_2$O/THF, −50° C. to ambient temperature
Scheme 3
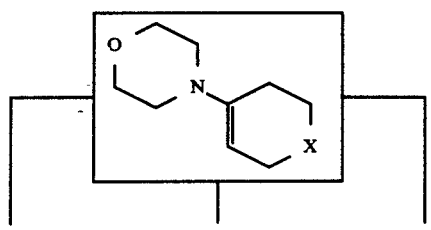

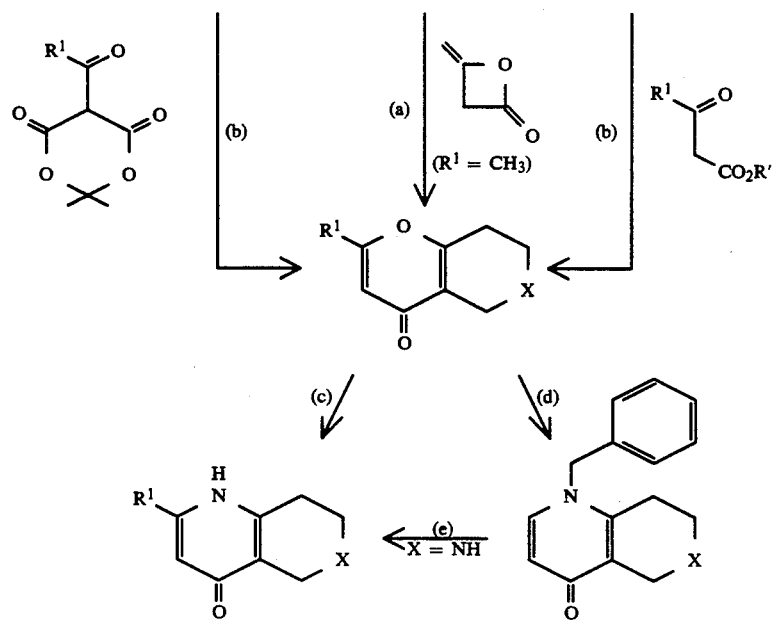
Scheme 4
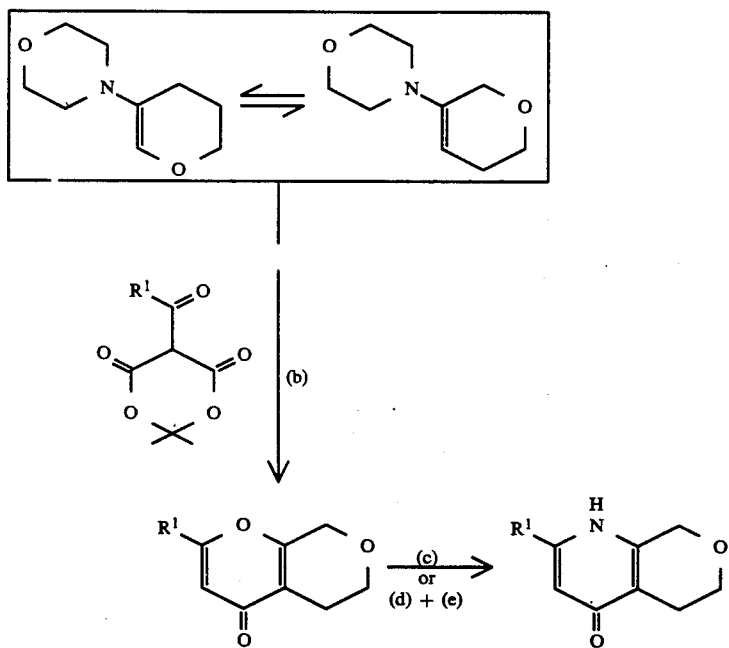
Note:
X is oxygen, sulphur or =NCH$_2$C$_6$H$_5$ (unless otherwise stated);
R' is lower alkyl
Reagents:
(a) reflux, dichloromethane
(b) heat together at elevated temperature, for example, in the range 100–150° C., optionally in a suitable solvent, for example, xylene
(c) aqueous ammonia, 120° C., sealed tube
(d) benzylamine, reflux
(e) hydrogenation, palladium on carbon, CH$_3$OH, aqueous HCl Scheme 5

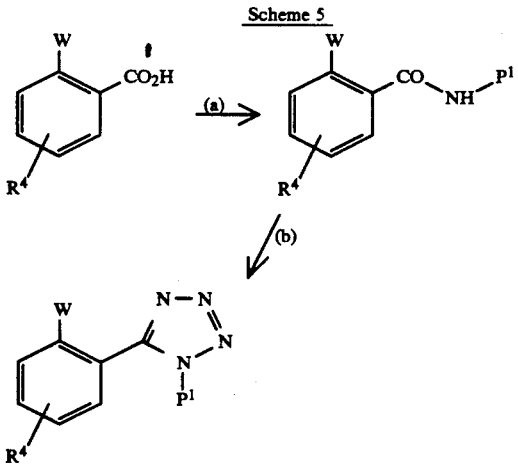

Reagents:
(a) thionyl chloride, DMF, toluene, 80° C.; then add to $P^1.NH_2$, toluene, NMP, ambient temperature
(b) (i) triethylamine, acetonitrile, DMF; (ii) thionyl chloride, 10° C.; and (iii) triethylamine, sodium azide, tetrabutylammonium bromide, 10° C. to ambient temperature

What we claim is:
1. A pyridine derivative of the formula I

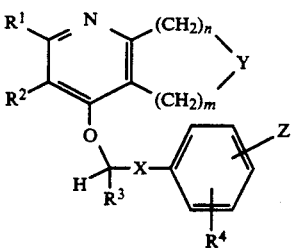

wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, (1-4C)alkoxy or phenyl substituent; $R^2$ is hydrogen, (1-8C)alkyl, (3-8C)cycloalkyl, (3-8C)cycloalkyl (1-4C)alkyl, carboxy, (1-4C)alkoxycarbonyl, (3-6C)alkenyloxycarbonyl, cyano, nitro, phenyl or phenyl(1-4C)alkyl; $R^3$ is hydrogen or (1-4C)alkyl, $R^4$ is independently selected from hydrogen, (1-4C)alkyl, (1-4C)alkoxy, halogeno, trifluoromethyl, cyano and nitro; n and m are independently selected from zero or the integers 1 to 4 such that the number of methylene groups in the ring containing Y is 2, 3 or 4, one of which methylene groups may optionally be replaced by a carbonyl group; Y is an oxygen atom, or a group of the formula —S-(O)$_p$— or —NR— in which p is zero or the integer 1 or 2, and R is hydrogen, (1-8C)alkyl, (1-8C)alkanoyl, carbamoyl, N-alkylcarbamoyl and di-(N-alkyl)carbamoyl of up to 7 carbon atoms, phenyl, phenyl(1-4C)alkyl or substituted (1-4C)alkyl, the latter containing one or more fluoro substituents; or R is a group of the formula -$A^1.A^2.B$ wherein $A^1$ is a direct bond or a carbonyl group; $A^2$ is (1-6C)alkylene; and B is selected from hydroxy, (1-4C)alkoxy, phenyloxy, phenyl(1-4C)alkoxy, pyridyl(1-4C)alkoxy, 4-morpholino(1-4C)alkoxy, phenylamino, amino, alkylamino and dialkylamino of up to 6 carbon atoms, (1-4C)alkanoylamino, (1-4C)alkylsulphonylamino, phenylsulphonylamino, sulphamoylamino (—NH.$SO_2$.$NH_2$), carboxamidomethylamino (—NH.$CH_2$.CO.$NH_2$), (1-4C)alkanoyloxy, phenylcarbonyloxy, aminocarbonyloxy (—O.-CO.$NH_2$), (1-4C)alkylaminocarbonyloxy, carboxy, (1-4C)alkoxycarbonyl, carbamoyl, N-alkylcarbamoyl and di-(N-alkyl)carbamoyl of up to 7 carbon atoms, (1-4C)alkanoyl, 4-morpholino, 1-imidazolyl and succinimido group; or B is a group of the formula -$A^3.B^1$ wherein $A^3$ is oxy, oxycarbonyl or imino and $B^1$ is a 5 or 6-membered saturated or unsaturated heterocyclic ring containing 1 or 2 nitrogen atoms and linked to $A^3$ by a ring carbon atom; or $A^3$ is oxycarbonyl and $B^1$ is a 4-morpholino group or a 5 or 6 membered saturated heterocyclic ring containing 1 or 2 nitrogen atoms, optionally bearing a (1-4C)alkyl group and linked to $A^3$ by a ring nitrogen atom; and wherein in $B^1$ the remainder of the ring atoms are carbon; X is phenylene optionally bearing a substituent selected from (1-4C)alkyl, (1-4C)alkoxy, halogeno, trifluoromethyl, cyano and nitro; Z is 1H-tetrazol-5-yl, —CO.NH.(1H-tetrazol-5-yl) or a group of the formula —$\overline{CO}$.$OR^5$ or —CO.NH.$SO_2$.$R^6$ in which $R^5$ is hydrogen or a non-toxic, biodegradable residue of a physiologically acceptable alcohol or phenol, and $R^6$ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or an N-oxide thereof; or a non-toxic salt thereof.

2. A compound as claimed in claim 1 wherein $R^1$ is hydrogen, methyl, ethyl, propyl, butyl, isobutyl, sec butyl, pentyl, hexyl, cyclopropyl, cyclopentyl, cyclohexyl, phenyl, fluoromethyl, trifluoromethyl, 2,2,2-trifluoroethyl, pentafluoroethyl, cyclopropylmethyl, cyclopentylmethyl, cyclohexylmethyl, 2-methoxyethyl, 2-ethoxyethyl, benzyl, 1-phenylethyl or 2-phenylethyl; $R^2$ is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl ethyl, carboxy, methoxycarbonyl, ethoxycarbonyl, propoxycarbonyl, allyloxycarbonyl, 2 methyl-2-propenyloxycarbonyl, 3-methyl-3-butenyloxycarbonyl, cyano, nitro, phenyl, benzyl, 1-phenylethyl or 2-phenylethyl; $R^3$ is hydrogen, methyl or ethyl; $R^4$ is independently selected from hydrogen, methyl, methoxy, ethoxy, ethyl, fluoro, chloro, bromo, iodo, trifluoromethyl, cyano and nitro; R is hydrogen, methyl, ethyl, propyl, butyl, isobutyl, sec-butyl, pentyl, hexyl, formyl, acetyl, propionyl, butyryl, pentanoyl, hexanoyl, carbamoyl, N-methylcarbamoyl, N-ethylcarbamoyl, N,N-dimethylcarbamoyl, N,N-diethylcarbamoyl, phenyl, benzyl, 1-phenylethyl, 2-phenylethyl, fluoromethyl, trifluoromethyl, 2,2,2-trifluoroethyl or pentafluoroethyl; or R is a group of the formula -$A^1.A^2.B$ wherein $A^1$ is a direct bond or a carbonyl group; $A^2$ is methylene, ethylene, trimethylene or tetramethylene; and B is selected from hydroxy, methoxy, ethoxy, isopropoxy, phenyloxy, benzyloxy, phenethyloxy, 2-pyridylmethoxy, 3-pyridylmethoxy, 4-pyridylmethoxy, 3-pyridylethoxy, 4-morpholinomethoxy, 4-morpholinoethoxy, phenylamino, amino, methylamino, ethylamino, butylamino, dimethylamino, diethylamino, dipropylamino, formamido, acetamido, propionylamido, methylsulphonylamino, ethylsulphonylamino, phenylsulphonylamino, sulphamoylamino, carboxamidomethylamino, acetyloxy, propionyloxy, phenylcarbonyloxy, aminocarbonyloxy, methylaminocarbonyloxy, ethylaminocarbonyloxy, carboxy, methoxycarbonyl, ethoxycarbonyl, propoxycarbonyl; carbamoyl, N-methylcarbamoyl, N-ethylcarbamoyl, N,N-dimethylcarbamoyl, N,N diethylcarbamoyl; formyl, acetyl, propionyl, 4-morpholino, 1-imidazolyl and succinimido; or B is a group of the formula -A³.B¹ wherein A³ is oxy, oxycarbonyl or imino and B¹ is pyrrolyl, imidazolyl, pyrazolyl, pyridyl, pyrazinyl, pyrimidinyl, pyridazinyl, pyrrolidinyl, imidazolidinyl, pyrazolinyl, piperidinyl or piperazinyl and linked to A³ by a ring carbon atom; or A³ is oxycarbonyl and B¹ is a 4-morpholino group or a pyrrolidinyl, imidazolidinyl, pyrazolinyl, piperidinyl or piperazinyl ring, optionally bearing a methyl or ethyl group and linked to A³ by a ring nitrogen atom; X is phenylene optionally bearing a substituent selected from methyl, ethyl, methoxy, ethoxy, fluoro, chloro, bromo, iodo, trifluoromethyl, cyano and nitro; R⁵ is hydrogen or a residue derived from a (1-6C)alkanol, or phenol or glycerol; and R⁶ is methyl, ethyl, propyl, isopropyl, butyl, pentyl, cyclobutyl, cycopentyl, cyclohexyl or phenyl; and wherein any of said phenyl moieties may be unsubstituted or bear one or two substituents selected from methyl, ethyl, methoxy, ethoxy, fluoro, chloro, bromo, cyano and trifluoromethyl.

3. A compound as claimed in claim 1 wherein Y is an oxygen atom, or a group of the formula —S(O)$_p$— or —NR— in which p is zero or the integer 1 or 2, and R is hydrogen, (1-8C)alkyl, (1-8C)alkanoyl or phenyl(1-4C)alkyl.

4. A compound as claimed in claim 1 wherein the sum of n and m is 3, and Z is 1H-tetrazol-5-yl attached ortho to the group X.

5. A compound as claimed in claims 1, 2, or 3 of the formula Ia

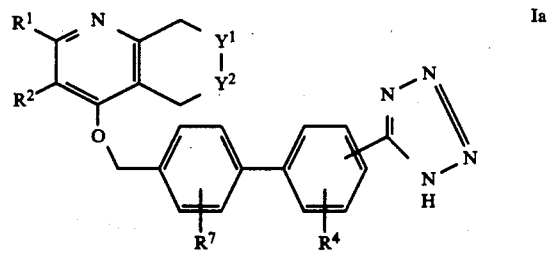

wherein one of Y¹ and Y² is an oxygen atom or a group of the formula —NR— and the other of Y¹ and Y² is a methylene group; and R⁷ is hydrogen, (1-4C)alkyl, (1-4C)alkoxy, halogeno, trifluoromethyl, cyano or nitro; and the non-toxic salts thereof.

6. A compound of the formula I selected from:
7,8-dihydro-2-ethyl-4-[(2'-(1H-tetrazol 5-yl)biphenyl-4-yl)methoxy]-5H-pyrano-[4,3 b]pyridine; and
6-benzyl-2-ethyl-5,6,7,8-tetrahydro-4-[(2'-(1H-tetrazol-5-yl)biphenyl-4-yl)methoxy]-1,6-naphthyridine; and the non-toxic salts thereof.

7. A salt as claimed in claim 1 which is selected from salts with acids forming physiologically acceptable anions and, for those compounds of formula I which are acidic, alkali metal, alkaline earth metal, aluminium and ammonium salts, and salts with organic bases affording physiologically acceptable cations.

8. A method for antagonising one or more of the actions of angiotensin II in a warm-blooded animal requiring such treatment which comprises administering to said animal an antagonistically effective amount of a compound of formula I, or a non-toxic salt thereof, as defined in claim 1.

9. A pharmaceutical composition which comprises a compound of the formula I, or a non toxic salt thereof, as claimed in claim 1, together with a pharmaceutically acceptable diluent or carrier.

10. A compound of the formula III

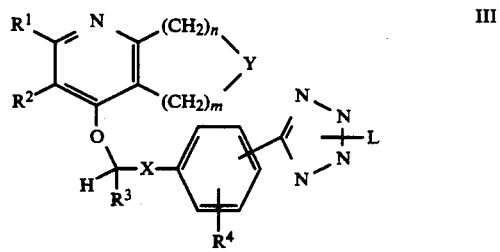

wherein R¹, R², R³, R⁴, n, m, X and Y have any of the meanings defined in claim 1, and L is a protecting group.

* * * * *